United States Patent
Balde

(10) Patent No.: US 10,517,826 B2
(45) Date of Patent: Dec. 31, 2019

(54) ANTHOSTEMA SENEGALENSE-BASED COMPOSITION FOR USE AS AN ANTI-AIDS DRUG

(71) Applicants: LABORATOIRE MICHEL IDERNE, Rosheim (FR); Aliou Mamadou Balde, Brussels (BE)

(72) Inventor: Aliou Mamadou Balde, Brussels (BE)

(73) Assignee: LABORATOIRE MICHEL IDERNE, Rosheim (FR)

( * ) Notice: Subject to any disclaimer, the term of this patent is extended or adjusted under 35 U.S.C. 154(b) by 19 days.

(21) Appl. No.: 15/508,468

(22) PCT Filed: Feb. 20, 2015

(86) PCT No.: PCT/FR2015/050413
§ 371 (c)(1),
(2) Date: Mar. 2, 2017

(87) PCT Pub. No.: WO2015/189487
PCT Pub. Date: Dec. 17, 2015

(65) Prior Publication Data
US 2017/0326070 A1 Nov. 16, 2017

(30) Foreign Application Priority Data
Jun. 10, 2014 (FR) ...................... 14 55226

(51) Int. Cl.
| | | |
|---|---|---|
| *A61K 36/47* | (2006.01) | |
| *A61K 9/14* | (2006.01) | |
| *A61K 31/4415* | (2006.01) | |
| *A61K 31/455* | (2006.01) | |
| *A61K 31/51* | (2006.01) | |
| *A61K 31/525* | (2006.01) | |
| *A61K 31/7072* | (2006.01) | |
| *A61K 33/04* | (2006.01) | |
| *A61P 31/18* | (2006.01) | |

(52) U.S. Cl.
CPC .......... *A61K 9/146* (2013.01); *A61K 31/4415* (2013.01); *A61K 31/455* (2013.01); *A61K 31/51* (2013.01); *A61K 31/525* (2013.01); *A61K 31/7072* (2013.01); *A61K 33/04* (2013.01); *A61K 36/47* (2013.01); *A61P 31/18* (2018.01)

(58) Field of Classification Search
None
See application file for complete search history.

(56) References Cited

U.S. PATENT DOCUMENTS

| 3,764,697 | A * | 10/1973 | Poeschel | ............... C07C 323/00 514/521 |
|---|---|---|---|---|
| 2012/0315327 | A1* | 12/2012 | Balde | ................... A61K 9/1652 424/452 |

OTHER PUBLICATIONS

Kone (Pharmaceutical Biology (2005), vol. 43, No. 1, pp. 72-78).*
International Search Report (ISR) dated May 26, 2015 in corresponding PCT application No. PCT/FR2015/050413 (with English translation; 4 pages).
International Preliminary Report on Patentability dated Dec. 15, 2016 in corresponding PCT application No. PCT/FR2015/050413 (with English translation; 11 pages).
Abreu P.M. et al., "Antimicrobial, antitumor and antileishmania screening of Medicinal Plants from Guinea-Bissau", Phytomedicine, vol. 6, No. 3, 1999, pp. 187-195 (in English; cited in the ISR).
Kone W. Mamidou et al., "Anthelmintic activity of medicinal plants used in northern Cote d'Ivoire against intestinal helminthiasis", Database Biosis [Online], Biosciences Information Service, Philadelphia, PA (USA), Jan. 2005, Database accession No. PREV200510007676; and Pharmaceutical Biology, vol. 43, No. 1, Jan. 2005, pp. 72-78 (in English; cited in the ISR).
Nikiema J.B. et al., "Strategie d'utilisation des substances naturelles dans la prise en charge des personnes vivant avec le VIH : experience du Burkina Faso" ["Strategy for use of natural substances in the treatment of individuals living with VIH: the experience of Burkina Faso"], Ethnopharmacologia, No. 43, Jul. 2009, pp. 47-51 (with English machine translation; 10 pages total; cited in the ISR).
Balde A.M. et al., "The Guinean traditional medicine in the treatment of HIV/AIDS", Retrovirology, vol. 3, No. Suppl. 1, 2006, p. P6, ; and International Meeting of The Institute of Human Virology; Baltimore, MD (USA), Nov. 17-21, 2006 (in English; 1 page; cited in the ISR).

* cited by examiner

*Primary Examiner* — Susan Hoffman
(74) *Attorney, Agent, or Firm* — Seckel IP, PLLC

(57) ABSTRACT

A pharmaceutical composition based on *Anthostema senegalense* is used as a drug in the treatment of HIV infection, AIDS and accompanying clinical manifestations. The composition can be used as an antiretroviral drug against HIV type 1 or HIV type 2. The composition includes polar and/or apolar plant extract of *Anthostema senegalense*, preferable obtained from the stem bark of *Anthostema senegalense*. The composition is preferably formulated in the form of microspheres produced using an extrusion and spheronization method, and then grouped together in capsules.

16 Claims, No Drawings

ANTHOSTEMA SENEGALENSE-BASED COMPOSITION FOR USE AS AN ANTI-AIDS DRUG

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to the use of *Anthostema-senegalense* in the preparation of a drug for the treatment of the infection with the Human Immunodeficiency Virus (HIV), of AIDS (Acquired Immunodeficiency Syndrome) and the accompanying clinical manifestations.

2. Description of Related Art Including Information Disclosed Under 37 CFR 1.97 and 37 CFR 1.98

In general, The acquired immunodeficiency syndrome, better known by its acronym AIDS, is a disease that results in a series of symptoms following the destruction of cells of the immune system by a retrovirus referred to as human immunodeficiency virus or HIV, two types are currently known: HIV-1 and HIV-2. AIDS is the last stage of the infection with this virus, which generally leads to the death of the people infected with opportunistic diseases.

The transmission of the AIDS virus occurs through sexual, blood, or mother-to-child transmission (through the placenta or during childbirth and/or breastfeeding). The viral particles of HIV present in the body fluids infect the cells of the immune system, in particular the T4 lymphocytes, which possess suitable receptors (the CD4 proteins).

As a result of the primary infection, the patient goes through an asymptomatic phase that can last for about ten years, during which he exhibits no symptoms of the disease, but during which his T4 lymphocytes and his macrophages are progressively destroyed by the HIV. At this stage, the individual has antibodies directed against the virus: he is said to be HIV-positive.

When his immune system is too weak, the symptoms of AIDS appear. Opportunistic diseases break out, such as for example tuberculosis, pneumonia or pneumocystis, but also herpes, or cancers (Kaposi's sarcoma, lymphomas, etc.), which can lead to the death of the patient.

The infection with the HIV virus is an epidemic that developed from the late 1970s and is now affecting the entire planet, both the developed countries and the developing countries, making this disease a global health problem. According to an estimate by the World Health Organization (WHO) dated December, 2012, more than 34 million people would be infected with the HIV virus worldwide, among whom 3.3 million children under 15 years of age. Sub-Saharan Africa alone would account for 69% of the cases. There would be approximately 2.5 million new infections annually, and 1.7 million deaths were reported in 2011.

Currently, it is not possible to cure AIDS and prevention, especially the use of a condom, remains the best option to fight the HIV virus, because there is currently no vaccine permitting to be protected against this virus.

There are nevertheless treatments that permit to slow down the evolution of the disease towards the AIDS stage. These treatments consist in taking one or preferably several antiviral molecules in combination for a higher efficiency. The triple therapies, which group three antiviral molecules, are generally recommended and are considered as being the most effective to contain the action of the virus and to stop its proliferation within the organism.

These treatments, which must be continued throughout the patients' lives, are very expensive and are therefore only very rarely available in the developing countries because the populations cannot bear the financial burden. In these countries, namely in Africa and in Asia, where the virus is very present, a vast majority of patients do nowadays not benefit from any effective treatment. Now, in the absence of a treatment, almost all HIV-infected patients progress to AIDS, and then to death.

In addition, even in countries where the triple therapies are prescribed, the latter are not effective on all patients. Indeed, there is a significant proportion of patients treated for whom this type of treatment remains ineffective (virological escape), even completely ineffective (therapeutic failure).

Furthermore, even when they are effective, these treatments have significant adverse effects as well as some toxicity, which reduces the patients' quality of life. Some patients, who no longer withstand these side effects, stop their treatment, whereas the latter must be followed very consistently in order to avoid making the virus resistant.

Finally, the molecules used in the triple therapies are often fragile molecules that require strict conditions of preservation, which is particularly problematic in hot and/or humid countries, namely in Africa and Asia.

In the developing countries, namely in Africa, it would be particularly interesting for all these reasons to have an effective and much cheaper treatment, obtained from local plants and in a form that does not raise preservation problems.

This is the aim of the invention, the aim of which is to provide an effective drug, which generates fewer side effects and the cost of which remains low compared to the cost of the triple therapies currently recommended in case of infection with the HIV.

This drug could also be provided in the developed countries as a complement to the current triple therapies for better efficiency or for treating undesirable side effects, or to replace them for economic reasons, to limit the side effects or in the cases where the conventional treatments are ineffective.

BRIEF SUMMARY OF THE INVENTION

In order to solve this technical problem, the invention teaches a pharmaceutical composition based on *Anthostema senegalense* for its use as a drug in the treatment of the infection with the Human Immunodeficiency Virus (HIV), of AIDS and the accompanying clinical manifestations.

This pharmaceutical composition can be used as an anti-retroviral drug against the HIV virus of the type 1 or the type 2.

Advantageously, the composition according to the invention has little or no side effects and is much cheaper than conventional drugs against AIDS. It is thus much better accepted by the patients for a regular long term treatment.

Moreover, its effect is enhanced by the other components present in the plant, which are mixed with the active ingredient when the therapeutic composition is produced. The totum thus has an improved effect with respect to the active ingredient in the isolated state.

In addition and as frequently occurs with natural extracts of not chemically modified plants, the active ingredient of the pharmaceutical composition of the invention has very few risks of overdosing.

Further features and advantages of the invention will become clear from reading the following detailed description.

BRIEF DESCRIPTION OF THE SEVERAL VIEWS OF THE DRAWINGS

None.

DETAILED DESCRIPTION OF THE INVENTION

*Anthostema senegalense* is a flowering plant of the Euphorbiaceae family.

This is a forest tree that can reach 30 m in height, with alternate, glabrous, simple, coriaceous leaves that are cuneiform at the base, with gutter-shaped petiole and deciduous leaf-like formation, elliptic-lanceolate tough foliage reaching up to 15 cm in length and 5-6 cm in width, cuneate at the base, acuminate at the top, penni-veins, 10-20 pairs of lateral veins. Its latex is white and its flowers are cyathiums grouped into small, from shortly pedunculate to subsessile axillary cymes. It has inflorescences in cyme, carrying at each branch an involucre of bracts enveloping numerous male flowers and one female flower. Its fruits are deeply tri-lobed capsules, containing three gray-yellowish-gray ovoid seeds spotted with brown of about 15 mm in length and 20-25 mm in width.

*Anthostema senegalense* grows in the forest fringes along the rivers. The species is endemic in West Africa where it can be found in the forest galleries in Guinea, Mali, Ivory Coast, Liberia, Senegal, Burkina Faso, Gambia, Guinea-Bissau, Sierra Leone, Benin and Nigeria. This plant is uncommon and in danger of extinction in some countries such as Ivory Coast due to the disturbance of its natural site.

For the preparation of the pharmaceutical composition according to the invention, the stem bark of *Anthostema senegalense* is preferably used, preferably after having been dried to remove the latex from same.

Although less advantageous, other parts of the *Anthostema senegalense* plant could also or alternatively be used to prepare the composition used according to the invention, such as for example its leaves, or its latex, although more toxic.

The pharmaceutical composition used according to the invention preferably comprises a plant extract of *Anthostema senegalense*. This plant extract is preferably a vegetable solution or a liquid plant extract and for example, according to its concentration, a mother tincture, a tincture officinalis or a liquid extract of *Anthostema senegalense*.

This plant extract of *Anthostema senegalense* is a polar extract, for example an aqueous, alcoholic or hydro-alcoholic; or apolar extract.

This plant extract is obtained by any suitable means and namely by extraction, preferably aqueous, alcoholic or hydro-alcoholic extraction, by maceration, infusion, decoction, percolation, digestion, leaching or the like.

A polar plant extract may for example be obtained by an extraction with methanol or ethanol.

An apolar plant extract may for example be obtained by extraction with dichloromethane ($CH_2Cl_2$), chloroform ($CHCl_3$) or with ethyl acetate ($CH_3COOC_2H_5$).

Another polar plant extract may for example be obtained by percolation with methanol through the marc resulting from the extraction with dichloromethane.

According to a preferred embodiment of the invention, a liquid plant extract is prepared from stem bark of *Anthostema senegalense* by means of a hydro-alcoholic extraction by a percolation technique with stirring. Its alcohol content is preferably between 30 and 70°.

By way of an example, an *Anthostema senegalense* mother tincture was prepared with an ethanol content of about 70% V/V from dry bark of *Anthostema senegalense* by exhaustive cold percolation followed by concentration under vacuum with the rotary evaporator.

The composition used according to the invention can adopt different galenic, preferably oral, forms. It can thus be for example in the form of infusettes containing for example about 5 grams of stem bark of roughly ground *Anthostema senegalense*.

It can also be in the form of tablets, preferably orodispersible tablets, of soft capsules, of granules, capsules, powder, ampoules, syrup, decoctate, fluid extract or any other suitable galenic form, preferably oral form, imaginable by those skilled in the art.

Preferably, the composition intended to be used according to the invention is formulated in the form of microspheres, also referred to as spheroids, preferably grouped into capsules in an amount corresponding preferably to a unit dose, for example a daily dose.

Thus, the benefits are the numerous advantages of this galenic form, namely in the medical field a quick release and a high bioavailability of the active ingredients and at practical level a great ease of use for the patient and a very little fragile and very stable form at long term, even under difficult storage conditions.

These microspheres can be made by various methods.

A first method consists for example in preparing a peripheral layer containing the plant extract of *Anthostema senegalense* around a neutral core, formed for example of a mixture of sugar and starch or of a sugar crystal, of mannitol or sorbitol.

The layer containing the plant extract of *Anthostema senegalense* can advantageously be prepared by coating, impregnation, spraying or projection, the active ingredient being to this end preferably mixed with a mounting agent or a binder.

According to a second preferred method, the microspheres or spheroids can be formed by extrusion and spheronization.

To this end, the plant extract of *Anthostema senegalense* is first mixed with an absorbing and adsorbent substance, preferably such as a natural or synthetic polymer, having plastic properties compatible with the extrusion and spheronization steps of the subsequent part of the method.

These are for example microcrystalline cellulose, microfine cellulose, a substituted weakly hydroxypropylated cellulose polymer, starch, modified starch, polysaccharides or any other suitable substance or mixture.

If the mixture is too dry, an aqueous or non-aqueous humidification liquid may also be added in order to obtain a homogeneous and malleable paste capable of undergoing the following steps of the method.

The humidifying liquid also serves as a vehicle for carrying and depositing the active ingredient until the core of the absorbing and adsorbent material in the micro-cavities of the polymer.

The manufacturing method then consists in extruding the wet mass through a die with calibrated orifices. In this way, compact filaments having a generally cylindrical and defined cross-section, referred to as "extrudates", are obtained.

These "extrudates" are then placed in a cylindrical apparatus referred to as "spheronizer" containing in the lower portion a key-shaped disc rotating at a varying and controlled speed. Under the effect of the centrifugal force exerted by the rotation of the rotating disc, the "extrudates" fragment regularly, then turn into spheres by a rolling-binding effect. The desired spheroids are thus obtained.

These two methods may also comprise at least a drying step and/or a calibrating step.

The drying can occur by slightly heating, for example at a temperature between 30 and 40° C. or by a simple exposure to the open air for a sufficient period of time.

Finally, the resulting spheroids may optionally be coated on the periphery with an outer film in order to protect them, for example from external moisture, heat, aggressive conditions of the body or a delayed effect.

Besides the plant extract of *Anthostema senegalense*, the composition intended for use according to the invention may in addition comprise one or several other suitable compounds or excipients, for example chosen from extracts from one or several other plants, vitamins, minerals, trace elements, aromas, mounting agents, binding compounds, sliding compounds, lubricating compounds, surfactants, sugars, lactose, sorbitol, mannitol, starches or modified starches, maltodextrins, carbonates, citrates, gelatin, polyvinylpyrrolidone, polysaccharides, cellulose derivatives, crosslinked sodium carboxymethylcellulose, microcrystalline cellulose, micro-fine cellulose, weakly substituted hydroxypropylated cellulosic polymers or any other suitable compound.

It may also comprise one or several compounds increasing the effectiveness of *Anthostema senegalense*, protecting it or helping its quick release.

It may also comprise, in combination, one or several other known antiviral or antiretroviral substances, namely one or several of those used within the framework of the conventional treatments against AIDS (triple therapies or the like). The composition according to the invention may thus comprise for example, besides *Anthostema senegalense*, zidovudine or azidothymidine (AZT), in order to reinforce its anti-HIV activity.

The following examples will permit to better illustrate the invention:

EXAMPLE 1

Spheroids were prepared by the extrusion and spheronization method described above, starting from an hydro-alcoholic extract of stem bark of *Anthostema senegalense*, prepared according to the European pharmacopoeia, with an ethanol content of 70% V/V and a dry residue of about 10%. These spheroids were grouped into 350 mg capsules.

For a 350 mg capsule:
Extract from *Anthostema senegalense* 350 ml dry residue equivalent 35 mg
micro-cellulose q.s.

The spheroids obtained were grouped into 350 mg capsules corresponding to a unit dose of composition, for a preferred dosage of three capsules per day.

EXAMPLE 2

Since taking vitamins and minerals is beneficial for improving the general health of immunosuppressed people, spheroids containing a mixture of vitamins and selenium in addition to the plant extract have been prepared.

These spheroids were prepared as above from the described hydro-alcoholic extract of stem bark of *Anthostema senegalense*.

Before extrusion and spheronization, vitamins and selenium were however added to this extract in the following proportions:

For 2.1 kg of extract:
vitamin PP: 70 g
vitamin B1: 8 g
vitamin B2: 8 g
vitamin B6: 8 g
selenium: 48 g The spheroids obtained were grouped into 350 mg capsules.

In order to demonstrate the anti-HIV properties of the composition intended to be used according to the invention, the present inventors conducted two studies: a series of in vitro tests and a clinical test, which permitted to conclude that a composition based on *Anthostema senegalense* was efficient. The results of these studies are summarized below.

In Vitro Tests:

An apolar extract and a polar extract of *Anthostema senegalense* were prepared by extraction with dichloromethane and methanol, respectively, from dried stem bark of *Anthostema senegalense*.

The efficacy of these extracts against the HIV virus was tested in vitro by measuring the median inhibitory concentration ($IC_{50}$) of these substances on the type 1 HIV virus (strain $III_B$) and on the type 2 virus (strain ROD). Their selectivity index was also measured in each case.

In order to serve as a control, three known antiretroviral molecules used in the treatment of the infection with HIV: nevirapine, dideoxycitidine and dideoxyinosine were also tested under the same conditions for comparison.

The results obtained are summarized in the table below:

| Sample tested | HIV-1 Strain $III_B$ | | HIV-2 ROD Strain | |
|---|---|---|---|---|
| | $IC_{50}$ (µg/ml) | Index of selectivity | $IC_{50}$ (µg/ml) | Index of selectivity |
| *Anthostema senegalense* apolar extract ($CH_2Cl_2$) | 0.250 | 119 | 0.0519 | 714 |
| *Anthostema senegalense* polar extract (MeOH) | 2.04 | 24 | 0.42 | 132 |
| Nevirapine | 0.047 | | >4.00 | |
| Dideoxycitidine | 0.29 | | 0.30 | |
| Dideoxyinosine | 2.89 | | 4.59 | |

It was found that the polar and apolar extracts of *Anthostema senegalense* exert in vitro a significant inhibition of each of both types of HIV (HIV-1 and HIV-2) tested with a satisfactory selectivity index.

The apolar extract has a very pronounced inhibitory activity against HIV-1, comparable to that of dideoxycitidine and better than that of dideoxyinosine. This activity is even better against HIV-2 for which it is significantly better than that of nevirapine, dideoxycitidine and dideoxyinosine.

The polar extract has a pronounced inhibitory activity against HIV-1, somewhat less good than that of nevirapine and dideoxycitidine, but slightly better than that of dideoxyinosine, and very pronounced against HIV-2 for which it is comparable to that of dideoxycitidine and significantly better than that of nevirapine and dideoxyinosine.

Clinical Test:

Six "naïve" HIV-positive patients, i.e. who never took an antiretroviral treatment against HIV, were treated for several months with an aqueous extract of *Anthostema senegalense* (patient 5) or a hydro-alcoholic extract of *Anthostema senegalense* (patients 2, 3 and 4) or also with infusettes containing dried stem bark of *Anthostema senegalense* (patients 1 and 6).

The aqueous extract was prepared by decoction for 15 minutes of 500 g dried and crushed bark of *Anthostema senegalense* in 1 liter of water, followed by filtration. A half water glass (about 10 cl) of this decoction was given daily to the patients treated with the aqueous extract.

The hydro-alcoholic extract was prepared at room temperature by percolation of 1 kg dried and ground bark of *Anthostema senegalense*, then by concentration of the extract obtained until one liter of fluid hydro-alcoholic extract was obtained. One teaspoon (i.e. about 5 ml) of this fluid extract was given daily to the patients treated with the hydro-alcoholic extract.

For the infusettes, 5 g dried and crushed bark of *Anthostema senegalense* were placed in each infusette. The patients treated with infusettes took one of them each day.

The CD4 cell count of these patients, corresponding to the number of CD4 cells per $mm^3$ of blood and reflecting the patient's T4 lymphocytes count, was measured monthly throughout the study.

The results obtained are summarized in the following table:

The composition according to the invention thus permitted to treat:
chronic diarrhea in three patients;
dermatoses in two patients;
dermal allergies in four patients.

The disappearance of these clinical manifestations of the infection with the HIV, by taking the composition used according to the invention, has permitted to considerably improve the quality of life of these patients.

Thus, in addition to a reduction of the infection with the HIV virus resulting into an increase in the CD4 cell count, an improvement in the overall health of the patients related to the disappearance of clinical manifestations related to the infection with the HIV virus is also observed.

The present inventors have also noticed that the composition based on *Anthostema senegalense* used according to the invention also has antifungal properties, namely against *Candida albicans*, a fungus responsible for candidiasis, which is a disease frequently found in patients infected with the HIV virus.

In vitro biological studies have thus permitted to show that the polar methanol extract from the stem bark of *Anthostema senegalense* has a significant activity with respect to *Candida albicans* with a median inhibitory concentration ($IC_{50}$) equal to 29.71 µg/ml, thus conferring to the composition according to the invention a therapeutic potential of interest for the treatment of candidiasis.

It is once again observed that the composition based on *Anthostema senegalense* used according to the invention also in addition advantageously permits to treat the clinical manifestations related to the infection with the HIV virus.

This composition offers an effective and much cheaper alternative to the current triple therapies for the treatment of the infection with the HIV virus, of AIDS and the accompanying clinical manifestations.

As set forth above, it can in addition be provided in a galenic form, which does not raise any preservation problems.

For all these reasons, the composition used according to the invention seems to be an extremely promising therapeutic solution for the developing countries.

| | CD4 count | | | | | | |
|---|---|---|---|---|---|---|---|
| | Patient 1 F, 32 years infusettes | Patient 2 F, 23 years hydro-alcoholic extract | Patient 3 M, 46 years hydro-alcoholic extract | Patient 4 F, 24 years hydro-alcoholic extract | Patient 5 M, 48 years aqueous extract | Patient 6 F, 30 years infusettes | Average ± SD |
| Month 1 | 134 | 118 | 276 | 142 | 218 | 110 | 166 ± 66 |
| Month 2 | 186 | 120 | 290 | 178 | 200 | 124 | 183 ± 62 |
| Month 3 | 180 | 140 | 325 | 132 | 264 | 116 | 192 ± 84 |
| Month 4 | 128 | 205 | 380 | 180 | 280 | 102 | 213 ± 103 |
| Month 5 | 150 | 280 | | 215 | | | 215 ± 65 |
| Month 6 | 162 | 200 | | 230 | | | 197 ± 34 |
| Month 7 | 180 | 290 | | | | | 235 ± 78 |

It was found that the treatment with the composition used according to the invention permitted to improve the CD4 cell count in five out of six patients after four to seven months of follow-up. Their CD4/CD8 cell ratio has also been improved.

In addition, an improvement and even disappearance of some clinical manifestations of the infection by the HIV have been noticed in these patients:

Obviously, the invention is not restricted to the preferred embodiments described above, since those skilled in the art can bring numerous modifications and imagine other variants without departing from the scope nor from the framework of the invention defined by the claims.

I claim:

1. A pharmaceutical composition for treatment of infection with Human Immunodeficiency Virus, comprising:
a plant extract of *Anthostema senegalense*, wherein the plant extract of *Anthostema senegalense* is an extract obtained by extracting dried stem bark of *Anthostema senegalense* with dichloromethane, wherein the pharmaceutical composition is formulated to contain an effective amount of the plant extract of *Anthostema senegalense* for treatment of at least one selected from the group consisting of infection with Human Immunodeficiency Virus, AIDS, and accompanying clinical manifestations thereof, wherein the plant extract of *Anthostema senegalense* is in the galenic form of microspheres produced by an extrusion and spheronization method.

2. The pharmaceutical composition, according to claim 1, wherein the plant extract of *Anthostema senegalense* is formulated as an antiretroviral drug for at least one selected from the group consisting of type 1 HIV virus and type 2 HIV virus.

3. The pharmaceutical composition, according to claim 1, further comprising at least one selected from the group consisting of plant extracts, vitamins, minerals, trace elements, aromas, binding compounds, glidants, lubricating compounds, surfactants, sugars, lactose, sorbitol, mannitol, starches, modified starches, maltodextrins, carbonates, citrates, gelatin, polyvinylpyrrolidone, polysaccharides, cellulose derivatives, crosslinked sodium carboxymethylcellulose, microcrystalline cellulose, micro-fine cellulose, antiviral substances, and antiretroviral substances.

4. The pharmaceutical composition, according to claim 3, further comprising at least one selected from the group consisting of zidovudine, azidothymidine, vitamin PP, vitamin B1, vitamin B2, vitamin B6, and selenium.

5. The pharmaceutical composition according to claim 1, wherein the microspheres of *Anthostema senegalense* are in an oral galenic form.

6. The pharmaceutical composition according to claim 1, wherein the microspheres are grouped into capsules.

7. A method of treatment of a patient infected with Human Immunodeficiency Virus, AIDS, comprising:
administering a pharmaceutical composition to a patient infected with Human Immunodeficiency Virus in need of such treatment,
wherein the pharmaceutical composition comprises a plant extract of *Anthostema senegalense*, wherein the plant extract of *Anthostema senegalense* is an extract obtained by extracting dried stem bark of *Anthostema senegalense* with dichloromethane, wherein the pharmaceutical composition is formulated to contain an effective amount of the plant extract of *Anthostema senegalense* so as to alleviate at least one selected from the group consisting of the infection, AIDS, and an accompanying clinical manifestation thereof.

8. The method according to claim 7, wherein the plant extract of *Anthostema senegalense* is formulated as an antiretroviral drug for at least one selected from the group consisting of type 1 HIV virus and type 2 HIV virus.

9. The method according to claim 7, wherein the pharmaceutical composition further comprises at least one selected from the group consisting of plant extracts, vitamins, minerals, trace elements, aromas, binding compounds, glidants, lubricating compounds, surfactants, sugars, lactose, sorbitol, mannitol, starches, modified starches, maltodextrins, carbonates, citrates, gelatin, polyvinylpyrrolidone, polysaccharides, cellulose derivatives, crosslinked sodium carboxymethylcellulose, microcrystalline cellulose, micro-fine cellulose, antiviral substances, and antiretroviral substances.

10. The method according to claim 9, wherein the pharmaceutical composition further comprises at least one selected from the group consisting of zidovudine, azidothymidine, vitamin PP, vitamin B1, vitamin B2, vitamin B6, and selenium.

11. The method according to claim 7, wherein the pharmaceutical composition is administered in an oral galenic form.

12. The method according to claim 11, wherein the pharmaceutical composition is administered in the galenic form of infusion from infusion-ready doses, microspheres, tablets, orodispersible tablets, soft capsules, granules, capsules, powder, ampoules, syrup, decoction or fluid extract.

13. The method according to claim 11, wherein the pharmaceutical composition is administered in the galenic form of microspheres produced by an extrusion and spheronization method.

14. The method according to claim 13, wherein the microspheres are grouped into capsules.

15. The method according to claim 7, wherein the plant extract of *Anthostema senegalense* is in the galenic form of microspheres produced by an extrusion and spheronization method.

16. The method according to claim 15, wherein the microspheres are grouped into capsules.

* * * * *